United States Patent [19]

Shimizu et al.

[11] Patent Number: 4,999,450
[45] Date of Patent: Mar. 12, 1991

[54] PROCESS FOR PREPARING ALPHA-(3-BENZYLPHENYL) PROPIONIC ACID DERIVATIVE

[75] Inventors: Isoo Shimizu; Yasuo Matsumura, both of Yokohama; Yutaka Arai, Tokyo, all of Japan

[73] Assignee: Nippon Petrochemicals Company, Limited, Tokyo, Japan

[21] Appl. No.: 499,191

[22] Filed: Mar. 23, 1990

Related U.S. Application Data

[63] Continuation of Ser. No. 283,480, filed as PCT JP88/00297 on Mar. 22, 1988, published as WU88/07032 on Sept. 22, 1988.

[30] Foreign Application Priority Data

Mar. 20, 1987 [JP] Japan .................................. 62-66466

[51] Int. Cl.$^5$ .............................................. C07C 69/76
[52] U.S. Cl. .................... 560/101; 562/491; 562/406; 568/429; 585/320; 585/323
[58] Field of Search ............... 560/101; 562/491, 406; 568/429; 585/320, 323

[56] References Cited

U.S. PATENT DOCUMENTS

| | | | |
|---|---|---|---|
| 3,641,074 | 2/1972 | Fenton | 562/406 |
| 3,641,127 | 2/1972 | Farge et al. | 260/516 |
| 4,423,021 | 12/1983 | Rollmann et al. | 423/333 |
| 4,536,595 | 8/1985 | Gardano et al. | 562/406 |
| 4,731,483 | 3/1988 | Shimizu et al. | 568/311 |

FOREIGN PATENT DOCUMENTS

| | | |
|---|---|---|
| 0074866 | 3/1982 | European Pat. Off. . |
| 0170147 | 2/1986 | European Pat. Off. . |
| 721597 | 3/1932 | France . |
| 391419 | 2/1964 | Japan .................................. 568/429 |
| 53-46943 | 4/1978 | Japan .................................. 568/429 |
| 55-36450 | 3/1980 | Japan . |
| 58-35145 | 3/1983 | Japan . |
| 63-233948 | 9/1988 | Japan .................................. 560/101 |

*Primary Examiner*—Bruce Gray
*Attorney, Agent, or Firm*—Scully, Scott, Murphy & Presser

[57] ABSTRACT

A process for preparing α-(3-benzylphenyl)-propionic acid or its derivative, a precursor of ketoprofen (trade name), which comprises dehydrogenating a by-product oil fraction formed in the production of ethylbenzene using synthetic zeolite as an alkylating catalyst, and carbonylating the product with carbon monoxide or the like. This precursor can be easily converted into ketoprofen, a useful medicine as an anti-inflammatory agent.

4 Claims, No Drawings

PROCESS FOR PREPARING ALPHA-(3-BENZYLPHENYL) PROPIONIC ACID DERIVATIVE

This application is a continuation of application Ser. No. 283,480, filed as PCT JP88/00297 or Mar. 22, 1988, published as WO88/07032 or Sept. 22, 1988 now abandoned.

DESCRIPTION

1. Technical Field

This invention relates to a novel compound of α-(3-benzylphenyl)propionic acid derivative through (3-vinylphenyl)phenylmethane. From this compound, it is possible to prepare easily and inexpensively α-(3-benzoylphenyl)propionic acid (trade name: ketoprofen) which is usefull as an anti-inflammatory agent or a pain-killing agent.

2. Background Art

It is disclosed in U.S. Pat. No. 3,641,127 that ketoprofen is prepared by oxidizing α-(3-benzylphenyl)propionic acid. However, in the same reference, the α-(3-benzylphenyl)propionic acid is produced by desulfuration of a sulfur-containing heterocyclic compound. In other words, it requires an expensive starting material as well as complicated reaction.

Because the oxidation of α-(3-benzylphenyl)propionic acid can be done easily, the problem in the preparation of ketoprofen have been easy and inexpensive preparation of α-(3-benzylphenyl)propionic acid.

It is, accordingly, the object of the present invention to provide a process for preparing highly pure ketoprofen inexpensively in a high yield.

DISCLOSURE OF INVENTION

That is, the present invention relates to a process for preparing α-(3-benzylphenyl)propionic acid derivative represented by the following formula (I), which process comprises the following steps (I) to (V).

Step (I): A process to prepare reaction product containing unreacted benzene, ethylbenzene, polyethylbenzene and heavier products by alkylating benzene with ethylene in the presence of ZSM-5 type synthetic zeolite catalyst;

Step (II): A process to recover (3-ethylphenyl)-phenylmethane by distillation as a fraction mainly containing components in the range of 288° to 295° C. (atmospheric pressure basis) in boiling point from the above reaction product;

Step (III): A process to dehydrogenate the above recovered fraction at temperature: 500° to 700° C. and pressure: reduced pressure to 5 kg/cm² in the presence of a dehydrogenation catalyst;

Step (IV): A process to carbonylate the above dehydrogenated fraction with carbon monoxide and hydrogen or water or a lower alcohol at reaction temperature: 40° to 200° C. in the presence of a transition metal complex carbonylation catalyst; and Step (V): A process to recover α-(3-benzylphenyl)-propionic acid derivative represented by the following formula (I) by distillation and/or extraction after the foregoing carbonylation.

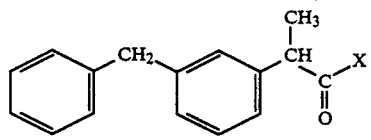

(wherein X is hydrogen, hydroxyl group or alkoxy group of $C_1$ to $C_4$).

In the following, the method of the present invention will be described in detail.

Alkylation

In the preparation of ethylbenzene, benzene is alkylated with ethylene in the presence of an alkylation catalyst to obtain an alkylation product mainly containing unreacted benzene, ethylbenzene, polyethylbenzene and heavier products. This alkylation can be done by known liquid phase alkylation method or gas phase alkylation method. The molar ratio of benzene to ethylene to be used can be about 25:1 to 1:5, preferably about 10:1 to 1:1.

The reaction is generally carried out in gas phase. In the gas phase reaction, materials for alkylation are reacted by passing them through, for example, ZSM-5 type catalyst in a temperature in the range of about 250° to 650° C., preferably about 300° to 550° C. and under a pressure in the range of atmospheric pressure to 100 kg/cm², preferably atmospheric pressure to 70 kg/cm² and at a space velocity of WHSV in the range of 1 to 500, preferably 1 to 300.

As a result of such alkylation, alkylation products of unreacted benzene, ethylbenzene, polyethylbenzene and heavier products are obtained. If desired, the contained catalyst is previously removed.

The by-product oil is obtained by removing unreacted benzene, ethylbenzene and at least a part of polyethylbenzene form the alkylation products described above.

The synthetic zeolite catalyst used in the present invention is crystalline synthetic aluminosilicate zeolite of 20 or higher in molar ratio of $SiO_2/Al_2O_3$ and the inlets of main pores thereof are composed of ten-membered oxygen rings. Such a zeolite is exemplified by ZSM-5 type synthetic zeolite having the inlets of main pores composed of ten-membered oxygen rings and further by zeolite zeta 1 and zeolite zeta 2. That is, the zeolites used in the present invention are characterized in the inlets of main pores composed of ten-membered oxygen rings. Conventional synthetic zeolites such as zeolite A and erionite have eight-membered oxygen rings, meanwhile, mordenite, zeolite X and zeolite Y have twelve-membered oxygen rings.

These conventional zeolites having eight-membered oxygen rings or twelve-membered oxygen rings are not suitable for use in the present invention owing to the difference in their structure.

Any of crystalline synthetic aluminosilicates as far as they are 20 or higher in molar ratio of $SiO_2/Al_2O_3$ and the inlets of main pores thereof are composed of ten-membered oxygen rings can be used as the crystalline synthetic zeolite in the present invention. Especially preferable one is ZSM-5 type synthetic zeolite known as ZSM-5, ZSM-11, ZSM-22, ZSM-23, ZSM-35, ZSM-38 and ZSM-48. These ZSM-5 type synthetic zeolites have the structural feature of that the inlets of main pores are composed of ten-membered oxygen rings. Especially preferable synthetic zeolite is ZSM-5. The compositions and methods for preparing these ZSM-5 type zeolites are disclosed in the following patent publications.

| ZSM-5: | U.S. Pat. No. 3,702,886 |
|---|---|
| ZSM-11: | U.S. Pat. No. 3,709,979 |
| | and Japanese Patent Pub. No. 53-23280 |
| ZSM-22: | U.S. Pat. No. 4,481,177 |
| ZSM-23: | U.S. Pat. No. 4,076,842 |

| | |
|---|---|
| | U.S. Pat. No. 4,490,342 |
| ZSM-35: | Japanese Laid-Open |
| | Patent Publication No. 53-144500 |
| ZSM-38: | U.S. Pat. No. 4,046,859 |
| ZSM-48: | U.S. Pat. No. 4,423,021 |
| Zeolite Zeta 1: | Japanese Laid-Open |
| | Patent Publication No. 51-67299 |
| Zeolite Zeta 2: | Japanese Laid-Open |
| | Patent Publication No. 51-67298 |

The synthetic zeolite having structural feature of the inlets of main pores being composed of ten-membered oxygen rings, usually has a high molar ratio of $SiO_2/Al_2O_3$ and the molar ratio is generally 20 or higher. In some case, the molar ratio of $SiO_2/Al_2O_3$ is very high, for example, the synthetic zeolite having the molar ratio as high as 1600 can be effective. Furthermore, it is possible to use in some case the zeolite having a value close to infinity in the molar ratio of $SiO_2/Al_2O_3$ close to infinity. Such "high-silica" zeolites are also included in the definition of the present invention. This molar ratio of $SiO_2/Al_2O_3$ can be determined by an ordinary analytical method such as atomic absorption spectrum analysis. This ratio is represented as close as possible to the ratio in the hard skeleton in zeolite crystal and the aluminum in cations or other forms contained in binder or channels are excluded.

The structure of ten-membered rings in the inlets of main pores generally confirmed by X-ray diffractiometry. For example, ZSM-5 type synthetic zeolite which is suitable as the catalyst in the present invention exhibit characteristic X-ray diffraction patterns particular to them (cf: the foregoing patent gazettes).

It is, however, possible to use values of constraint indexes in place of the X-ray diffractiometry. That is, the ten-membered oxygen ring in the present invention can be defined as the zeolite of 1 to 12 in constraint index. By the way, the constraint index is described with practical determination method in Japanese Laid-Open Patent Publication No. 56-133223. This index shows the degree that the fine pore structure of zeolite crystal restrains the contiguity of molecules having a cross sectional area larger than that of n-paraffin. In the determination, as disclosed in the same reference, n-hexane and 3-methylpentane are adsorbed by zeolite under certain conditions and the index is calculated from the adsorbed values.

Typical values of constraint indexes are as follows:

| | Constraint Index |
|---|---|
| ZSM-5 | 8.3 |
| ZSM-11 | 8.7 |
| ZSM-35 | 4.5 |
| Amorphous Silica-Alumina | 0.6 |

The method for preparing zeolite in the present invention will be described with reference to the synthesis of ZSM-5. A mixture containing the reactants of tetrapropylammonium hydroxide or tetra-n-propylammonium bromide, sodium oxide, aluminum oxide, silicon oxide and water, is prepared in the first place. The composition may be made with the range as disclosed in the foregoing reference. This reaction mixture is subjected to hydrothermal synthesis by heating. After the synthesis, the obtained crystal is baked in the air to obtain zeolite ZSM-5 catalyst. Aluminum oxide is used herein, however, it is also proposed to synthesize ZSM-5 containing substantially no aluminum atom. In the above method, tetrapropylammonium hydroxide or tetra-n-propylammonium bromide is used, however, it is proposed as the method for synthesizing ZSM-5 to use several other organic cations or organic compounds as their precursors in place of them. Such compounds are exemplified by ammonia, trialkylmethylammonium cation, triethyl-n-propylammonium cation, $C_2$ to $C_9$ primary monoalkylamine, neopentylamine, di- and trialkylamine, alkanolamine, $C_5$ to $C_6$ alkyldiamine, $C_3$ to $C_{12}$ alkylenediamine, ethylenediamine, hexamethylenediamine, $C_3$ to $C_6$ diol, ethylene or propylene glycol, 1,4-dimethoxycyclohexane, hydroquinone, ethylene oxide and ammonia, n-dodecylbenzene sulfonate, cyclopentadienyl phthalocyanine complex, 2-aminopyridine, ethylene glycol dimethyl ether, dioxane, dioxolan, tetrahydrofuran, and carboxylic acids such as tartaric acid.

Furthermore, it is also proposed that, without adding organic cation or organic compound as a precursor of it as referred to above, ZSM-5 is added as the seeds in crystallization.

The zeolite used for the reaction contains metallic ions such as sodium ions which come from the reaction materials in synthesis. Besides the alkali metals such as sodium, it can be used which is ion exchanged by other metals of alkaline earth metals such as calcium and magnesium and other tri-valent metallic ions. Furthermore, crystalline synthetic aluminosilicate zeolite which is modified by impregnating it with magnesium, boron, potassium, phosphorus or their compounds, for example, ZSM-5 type zeolite, can also be used. These ion exchange and modification can be carried out according to conventional methods.

As described above, the crystalline synthetic zeolite of the present invention can contain various kinds of metals. However, the synthetic zeolite which is desirable for the method of the present invention is the so-called hydrogen-type zeolite (HZSM-5) or acid-type zeolite in which the metallic ions are exchanged by hydrogen ions. Typical hydrogen-type zeolite is prepared by a process such that the catalyst containing organic cations in the catalyst preparation is heated for instance at about 540° C. for 1 hour in an inert atmosphere and it is then subjected to ion exchange with an ammonium salt or a mineral acid such as hydrochloric acid, and it is baked, for example, at about 540° C. to activate it to obtain the what is called hydrogen-type zeolite.

If desired, the zeolite may be further subjected to steam treatment or coking treatment.

Through the above described process, benzene is alkylated with ethylene to obtain a reaction mixture of unreacted benzene, ethylbenzene, polyethylbenzene and heavier components. This heavier components contains (3-ethylphenyl)phenylmethane as well as other tarry substances.

A fraction containing (3-ethylphenyl)phenylmethane is recovered from the above reaction product directly by preferably reduced pressure distillation or by recovering the heavier components and then distilling it again. Anyhow, the fraction containing (3-ethylphenyl)phenylmethane is recovered as a fraction mainly containing the components of 288 to 295° C. in boiling point (atmospheric pressure basis).

Incidentally, the above reaction for alkylation is exemplified by the ethylbenzene preparation using the zeolite catalyst made by Mobil Oil Corp., which is widely put into practice in industry, the ethylbenzene is used for preparing styrene by dehydrogenation.

Dehydrogenation Reaction

In the present invention, the fraction containing the above (3-ethylphenyl)phenylmethane is subjected to dehydrogenation in the presence of a dehydrogenation catalyst. As the dehydrogenation catalyst for this purpose, the catalyst which is used in the dehydrogenation of ethylbenzene to prepare styrene can be used.

That is, catalysts consisting of iron oxide, chromium oxide or mixture thereof can be used.

For example, there are chromia-alumina catalyst and iron oxide catalyst. These catalysts can be used together with a promoter such as potassium carbonate or the oxide of cerium, molybdenum or vanadium.

Because the dehydrogenation is an equilibrium reaction, with regard to the pressure as a reaction condition for dehydrogenation, the reaction can proceed faster in a lower pressure. Further, the reaction proceeds faster in higher temperatures because it is an intense endothermic reaction. Accordingly, the reaction temperature is generally selected from the range of 500° to 700° C., and preferably 550° to 650° C. At a temperature below 500° C., the dehydrogenation reaction cannot substantially proceed. On the other hand, temperatures above 700° C. is not desirable because side reaction such as decomposition is caused to occur. The reaction pressure is from a reduced pressure to 5 kg/cm$^2$, and preferably from a reduced pressure to 3 kg/cm$^2$. In general, excess steam is used as a heating medium.

The reaction time length in a continuous flow system is selected from the range of 0.01 to 10 as LHSV.

After the reaction, (3-vinylphenyl)phenylmethane is obtained by distillation, preferably under a reduced pressure.

(3-Vinylphenyl)phenylmethane which is produced by this dehydrogenation can be separated relatively easily by distillation because the boiling point of this compound is higher than those of saturated compound contained in the starting material.

However, the difference in boiling points of saturated compounds and those of unsaturated compounds.

Therefore, (3-ethylphenyl)phenylmethane is contained in the fraction containing (3-vinylphenyl)phenylmethane, however, it is not necessary to remove the (3-vinylphenyl)phenylmethane by means of more elaborate reduced pressure distillation or refining, and the dehydrogenation product can be used for the next carbonylation as it stands or with removing only lighter or heavier by-products which is by-produced in dehydrogenation, by distillation. The fraction containing (3-vinylphenyl)phenylmethane to be fed to the carbonylation step is generally used as a fraction mainly containing components of 290° to 300° C. in boiling point on the atmospheric pressure basis.

The carbonylation step will be described. In the following, both the hydroformylation by supplying and reacting with carbon monoxide and hydrogen and the hydroesterification by supplying and reacting with carbon monoxide and water or a lower alcohol are sometimes called as carbonylation as a whole.

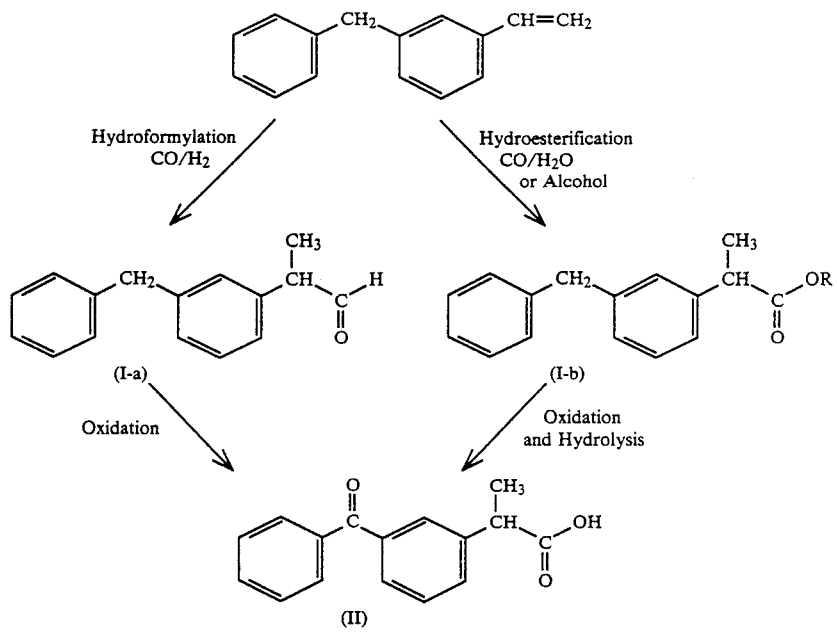

In the case that (3-vinylphenyl)phenylmethane is reacted with hydrogen and carbon monoxide in the presence of a transition metal carbonylation catalyst (hydroformylation), α-(3-benzylphenyl)propionaldehyde of the formula (I-a) is obtained (X=H in formula (I)). By oxidizing its methylene group and formyl group, ketoprofen of the formula (II) is obtained.

Furthermore, when (3-vinylphenyl)phenylmethane is reacted with water or an alcohol and carbon monoxide in the presence of a transition metal carbonylation catalyst (hydroesterification), α-(3-benzylphenyl)propionic acid or its ester the formula (I-b) is obtained (X=OH or OR in formula (I)). By oxidizing its methylene group and hydrolyzing if necessary, ketoprofen of the formula (II) is obtained.

The transition metal catalysts used for the carbonylation are transition metals such as Ni, Co, Fe, Mo, Pd, Pt, Rh, Ir, Ru and Re. Among them, precious metals such as Pd, Pt, Rh, Ir and Ru are preferable. As the transition metals, those having oxidation numbers from 0 to the highest numbers can be used. Usable complexes are those having ligands of halogen atoms, trivalent phosphorus compounds, π-allyl group, amines, nitriles, oximes, olefins, hydrogen, or carbon monoxide.

The transition metal complex catalysts are exemplified by bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine acetate complex, bistriphenylphosphine dinitrate complex, bistriphenylphosphine sulfate complex, tetrakistriphenylphosphine complex; and chlorocarbonyl bistriphenylphosphine complex, hydridocarbonyl tristriphenylphosphine complex, bischlorotetracarbonyl complex and dicarbonyl acetylacetonate complex in which a part of ligands are carbon monoxide.

Furthermore, the compounds which produce the above metal complexes in the reaction system can be also used by feeding it into the reaction system. That is, phosphine, nitrile, allyl compound, amine, oxime, olefin or carbon monoxide which is able to be the ligands to the oxides, sulfates or chlorides of the above transition metals, are simultaneously added into the reaction system.

The above phosphines as ligands are exemplified by triphenylphosphine, tritolylphosphine, tributylphosphine, tircyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclododecatriene.

The use quantity of a complex catalyst or a compound which can produce a complex is 0.0001 to 0.5 mole, preferably 0.001 to 0.1 mole to one mole of (3-vinylphenyl)phenylmethane.

When the compound which produces a complex is used, the addition quantity of the compound to form ligands is 0.8 to 10 moles, preferably 1 to 4 moles, to one mole of the compound to produce a complex.

Furthermore, for the purpose of improving the rate of reaction, it is possible to add inorganic halides such as hydrogen chloride and boron trifluoride or organic iodide such as methyl iodide.

When these halides are added, the quantities of them are 0.1 to 30 times by mole, preferably 1 to 15 times by mole, as halogen atoms to 1 mole of the complex catalyst or the compound to produce a complex. Even though it depends upon the kind of used catalyst, if the addition quantity is less than 0.1 mole, the effect of the addition cannot be observed sometimes. If the addition quantity exceeds 30 times by moles, not only the catalytic activity is lowered but also halogen atoms are added to the double bonds of (3-vinylphenyl)phenylmethane which fact is a bar to the aimed reaction.

The carbonylation is carried out at 40° to 150° C. in reaction temperature, preferably 55° to 130° C. If the reaction temperature is below 40° C., the rate of reaction is very low which is not acceptable in industrial processes. On the other hand, if the reaction temperature is above 150° C., it is not desirable because the side reactions of polymerization, the addition of hydrogen, the addition of alcohol and the decomposition of complex catalyst are caused to occur.

As far as the reaction pressure is 5 kg/cm$^2$ or above, it can be selected arbitrary. When the reaction pressure is lower than 5 kg/cm$^2$, the rate of reaction is very low, which cannot be adopted practically. When the reaction pressure is higher, the reaction proceeds faster. However, a too high pressure necessitates a very high pressure resistance for a reaction vessel, so that there is naturally a limit in view of the designing of reaction equipment. Accordingly, it is sufficient that the pressure is not higher than 800 kg/cm$^2$ in a practical view point.

In the hydroformylation in which carbon monoxide is used together with hydrogen, the reaction is continued until the lowering of pressure owing to the absorption of the mixed gas of carbon monoxide and hydrogen, is not observed. The reaction time of 4 to 20 hours is generally sufficient.

The carbon monoxide and hydrogen that are necessary for the reaction can be fed either separately or by mixing them previously. The molar ratio of carbon monoxide and hydrogen to be fed into the reaction system can be selected arbitrary. In this carbonylation reaction, carbon monoxide and hydrogen are consumed or absorbed accurately at a molar ratio of 1:1. Accordingly, because a component which is supplied in excess remains unreacted, the reaction can be proceeded again if the other component is supplied at the time when the lowering of pressure is not observed. Even though it will depend upon the size of reaction vessel and the mode of reaction, it is generally most effective that carbon monoxide and hydrogen are fed in a molar ratio of 1:1.

After the hydroformylation, the reaction product is subjected to separation, preferably by distillation under a reduced pressure and the aimed product of α-(3-benzylphenyl)propionaldehyde (formula I-a) and catalyst can be separated quite easily. The recovered complex catalyst can be used again for the hydroformylation process.

In the hydroesterification in which carbon monoxide is used together with water or alcohol, when (3-vinylphenyl)phenylmethane is reacted in the presence of water, a carboxylic acid in which the X in the formula (I) is a hydroxyl group can be obtained. Further, when it is reacted with a lower alcohol in which the alkyl group has 1 to 4 carbon atoms, an ester of the formula (I) in which the X is the alkoxy group of the lower alcohol can be obtained. For example, methyl ester is obtained with methyl alcohol.

The alcohols are lower alcohols having 1 to 4 carbon atoms, which are exemplified by methyl alcohol, ethyl alcohol, n-propyl alcohol, isopropyl alcohol, n-butyl alcohol, sec-butyl alcohol, tert-butyl alcohol and isobutyl alcohol. Among them, methyl alcohol is preferable.

After the hydroesterification, the reaction product is subjected to separation preferably by distillation under a reduced pressure or by extraction, and the aimed product of α-(3-benzylphenyl)propionic acid or its ester (formula I-b) and catalyst can be separated quite easily. Of course, both the distillation and extraction can be used for separation. The recovered complex catalyst can be used again.

After the carbonylation of the step (IV), α-(3-benzylphenyl)propionic acid derivative of the formula (I) is recovered by distillation or extraction or both. The separation of unreacted (3-ethylphenyl)phenylmethane contained in the fraction from the dehydrogenation step from (3-vinylphenyl)phenylmethane is difficult before the carbonylation, however, after the carbonylation, the separation can be done quite easily. Therefore, (3-ethylphenyl)phenylmethane is recovered after the carbonylation by distillation or extraction, and it is preferably recycled as a starting material to the dehydrogenation step (III). On this occasion, it can be recycled together with (3-vinylphenyl)phenylmethane to the dehydrogenation step. That is, as described above, it is not especially necessary for the dehydrogenation step to carry out the separation of unreacted substances and the refining of aimed product which are generally done in ordinary processes and it is sufficient that the refining only to remove decomposition products by side reaction and polymeric substance is done.

The thus obtained carbonylation product of α-(3-benzylphenyl)propionic acid derivative is then oxidized, for example, according to the disclosure of U.S. Pat. No. 3,641,127 to obtain ketoprofen easily.

In the following, the oxidation is described.

In the oxidation of α-(3-benzylphenyl)propionaldehyde (formula I-a) obtained in the carbonylation using hydrogen, the formyl group and the methylene group between two phenyl groups are oxidized. It is possible to oxidize both the methylene group and formyl group simultaneously in one step reaction. Meanwhile, it is also possible to oxidize the methylene group and then to oxidize the formyl group. Furthermore, it is also possible that the order of oxidation is reversed. When the formyl group is oxidized later, the oxidation is carried out after the formyl group is blocked by a known method.

When the methylene group is firstly oxidized, α-(3-benzoylphenyl)propionaldehyde is formed. When the formyl group is firstly oxidized, α-(3-benzylphenyl)propionic acid of the formula (I-b) is obtained.

oxidation to produce α-(3-benzylphenyl) propionic acid and it is then oxidized.

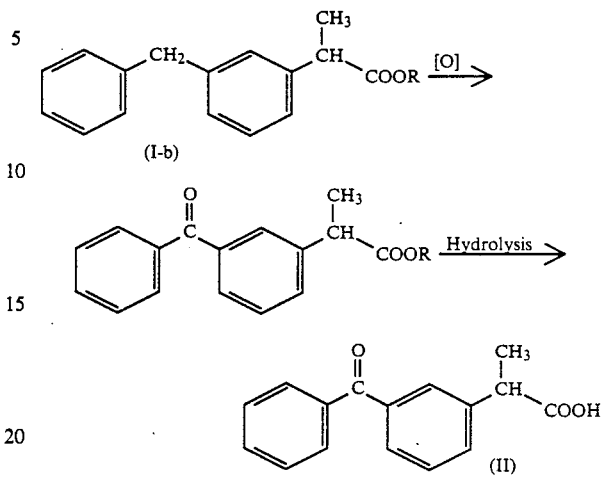

The above oxidation is exemplified by the oxidation using molecular oxygen in the presence of an oxidation catalyst and the oxidation using an oxidizing agent such as permanganate, manganese dioxide, chromate, bichromate, lead tetraacetate, periodate, ruthenium tetraoxide, osmium tetraoxide, hydrogen peroxide, selenium dioxide, chlorite or hypochlorite, ozone and mixtures of them.

The necessary quantity of the oxidizing agent such as permanganate is at least 1 equivalent, preferably more than 1.5 equivalent relative to the reaction material. There is no upper limit with regard to the use quantity, however, a quantity more than 10 equivalent is not desirable because it is uneconomical. The reaction tem-

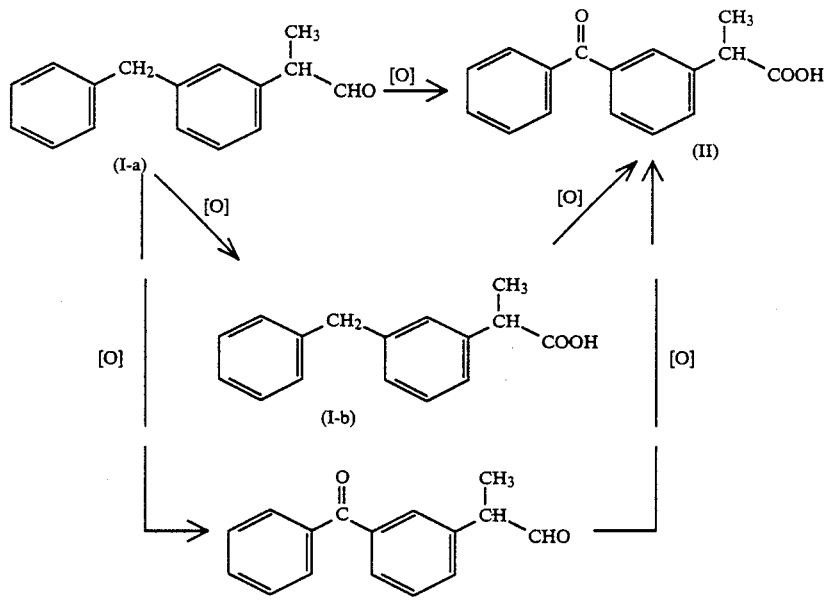

Furthermore, by oxidizing the α-(3-benzylphenyl)-propionic acid or its alkyl ester of the formula (I-b) obtained from hydroesterification using water or alcohols, and by hydrolyzing if necessary, ketoprofen of α-(3-benzoylphenyl)propionic acid of the formula (II) can be easily obtained. When an ester is obtained by hydroesterification, it may be hydrolyzed before the perature of oxidation using an oxidizing agent is 0° to 200° C., preferably 30° to 150° C. At a reaction temperature below 0° C., the reaction cannot proceed and at a temperature above 200° C., it is not desirable because side reaction products are produced and the selectivity for the aimed product is lowered remarkably.

The catalyst used in the oxidation with molecular oxygen are exemplified by the salts of metals and mixtures of them, which metals are selected from the groups VI-B, VII-B and VIII of the periodic table such as chromium, manganese, tungsten, molybdenum, platinum, palladium, cobalt, nickel, iron, rhodium and ruthenium. Among them, the salts of cobalt, iron, manganese and chromium are preferable. As the salts, for example, the salts of saturated carboxylic acid such as naphthenic acid are preferable. The suitable quantity of a catalyst to be used is 0.05 to 10% by weight to the quantity of reactants. As the molecular oxygen, pure oxygen or the air can be used. Furthermore, it is possible to supply the reaction system with a mixture of pure oxygen and other inert gases.

The reaction temperature in the oxidation using molecular oxygen is 30° to 250° C., and preferably 50° to 200° C. In the case that the reaction temperature is lower than 30° C., the rate of reaction is very low, and in the case that the reaction temperature is above 250° C., the selectivity to the aimed product is seriously lowered, both of which are not desirable.

In order to improve the efficiency in the contact with an oxidizing agent, a solvent can be used. Such a solvent is exemplified by water, acetone, alcohols such as tert-butyl alcohol, glacial acetic acid, acetic acid, isooctane, benzene, chloroform and pyridine and the mixture of them.

After the oxidation, the oxidizing agent or oxidation catalyst is separated by, for example, filtration, or the reaction mixture is extracted with an organic solvent such as benzene, ethyl acetate or chloroform. After that, highly pure α-(3-benzoylphenyl)propionic acid, ketoprofen, is obtained by the conventional distillation or recrystallization. When the oxidation product is an ester, it is hydrolyzed by an ordinary method, which is followed by refining to obtain easily highly pure α-(3-benzoylphenyl)propionic acid.

As described above, according to the method of the present invention, the α-(3-benzylphenyl)propionic acid derivative as a precursor of ketoprofen can be easily prepared in high purity and inexpensively from the heavier by-product oil obtained in the ethylation of benzene using ZSM-5 type synthetic zeolite catalyst. From this α-(3-benzylphenyl)propionic acid derivative, ketoprofen is easily prepared by oxidizing it or, if necessary, by hydrolyzing it before or after the oxidation.

BEST MODE FOR CARRYING OUT THE INVENTION

In the following, the present invention is described in more detail.

EXPERIMENT 1

Alkylation

To a stainless steel-made continuous flow reaction vessel was added 100 g of a synthetic zeolite ZSM-5 (H-type, 60 in molar ratio of $SiO_2/Al_2O_3$) and alkylation of benzene with ethylene was carried out under the following conditions.

| | |
|---|---|
| Reaction Temperature: | 450° C. |
| Pressure: | Atmospheric pressure |
| Ethylene/Benzene: | 0.2 (by molar ratio) |
| WHSV: | 4.5 |

The obtained reaction mixture was distilled and heavier components were recovered in a yield of 2.5% by distilling off the unreacted benzene, ethylbenzene and polyethylbenzene.

Then, a fraction (A) of 288° to 293° C. in boiling range (atmospheric pressure basis) was obtained from the recovered heavier components by reduced pressure distillation.

This fraction contained (3-ethylphenyl)phenylmethane. According to analysis, the content of (3-ethylphenyl)phenylmethane was 87% by weight. (Dehydrogenation)

The above fraction was dehydrogenated under the following conditions using steam as a heating medium.

| | |
|---|---|
| Catalyst: | Made by Nissan Girdler Co., Trademark: G-64C (Iron oxide catalyst with promoters of potassium carbonate and chromium oxide) |
| Temperature: | 600° C. |
| LHSV: | 2.0 |
| Steam/Hydrocarbon: | 2.0 (by molar ratio) |

After the dehydrogenation, a fraction of 283° to 298° C. in boiling range (atmospheric pressure basis) was obtained by distilling under reduced pressure likewise. According to analysis, the content of (3-vinylphenyl)phenylmethane was 48% by weight.

The IR spectrum and NMR spectrum of this product were compared with those of the (3-vinylphenyl)phenylmethane which was prepared by the following method. The results were the same.

Even though the above fraction contained unreacted (3-ethylphenyl)phenylmethane, however, the fraction was used in the following carbonylation step without removing the compound.

REFERENCE PREPARATION EXAMPLE

Another Synthesis of (3-Vinylphenyl)phenylmethane

To a 2 liter three-neck flask equipped with a reflux condenser and a stirrer were added 28 g (1.15 moles) of metallic magnesium and 50 ml of tetrahydrofuran dried with sodium metal and it was stirred at room temperature. A solution of 183 g of 3-vinylbenzene bromide (1.02 moles) in 500 ml of dry tetrahydrofuran was dropped slowly over 2 hours. The reaction temperature was kept at 80° C.

After the dropping, it was stirred for further 1 hour at 80° C. The thus obtained Grignard reagent was dropped slowly over 2 hours to a solution of 171 g (1.0 mole) of benzyl bromide and 5.5 g of $NiCl_2(Ph_2P(CH)_3PPh_2)$ in 500 ml of dry ether and the stirring was continued for further 1 hour at 35° C. The reaction mixture was then poured into ice water. After that, it was put into the separatory funnel to recover an oily layer and ether and tetrahydrofuran were evaporated off under reduced pressure. Thereby obtaining (3-vinylphenyl)phenylmethane in a yield of 60%.

The analytical data on the thus obtained product are shown in the following:

Boiling Point: 108.5–110.5° C./0.5–1 mmHg

IR: (Neat) $cm^{-1}$ 3040, 2930, 1635, 1600, 1500, 1460, 995, 910, 790, 710, 700

$^1$H-NMR: ($CCl_4$, δ ppm): 6.70–7.70, (9H Multiplet), 6.30–6.60, (1H Quadruplet), 5.40–5.70, (1H Doublet), 5.00–5.15, (1H Doublet), 3.80, (2H Singlet).

Elemental Analysis: (as $C_{15}H_{14}$) Calculated: C: 92.78%, H: 7.22%, Found: C: 92.80%, H: 7.20%.

Ketoprofen was prepared by using the fraction containing (3-vinylphenyl)phenylmethane as a starting material which was obtained in the foregoing Experiment 1.

EXPERIMENT 2

Synthesis of α-(3-Benzylphenyl)propionic Acid
(Formula I, X=—OH)

To a 500 ml autoclave with a stirrer were added 40 g of the fraction containing (3-vinylphenyl)phenylmethane obtained in the above Experiment 1, 75 g of 10% aqueous solution of hydrochloric acid, 0.8 g of bistriphenylphosphine dichloropalladium and 80 ml of benzene as a reaction solvent. The pressure was raised to 100 kg/cm$^2$ with carbon monoxide at room temperature. The temperature was then raised to 100° C. and the pressure was further raised to 300 kg/cm$^2$ with carbon monoxide. The reaction was continued until the absorption of carbon monoxide was ceased.

After the reaction, benzene layer was separated by cooling and extraction was carried out 3 times with 50 ml of 5% aqueous solution of sodium hydroxide. Hydrochloric acid was added until the pH value of the sodium hydroxide solution became 2 and it was extracted with chloroform. The chloroform was removed under reduced pressure to obtain 18 g yellow crude crystal of α-(3-benzylphenyl)propionic acid.

The above product was refined by recrystallization and the melting point, IR spectrum and NMR spectrum of the obtained sample were measured, which coincided with the values on references.

EXPERIMENT 3

Synthesis of α-(3-Benzoylphenyl)propionic Acid
(Ketoprofen) - (1).

A solution of 24 g of α-(3-benzylphenyl)propionic acid obtained in Experiment 2 in 200 ml of benzene was dispersed in 200 ml of water, to which 2 liter of 1.6% solution of potassium permanganate was added dropwise with stirring. After the dropping, stirring were continued for about 10 hours at room temperature. The mixture was then acidified with concentrated sulfuric acid and it was treated with 30 g of sodium sulfite. Water was then added to the reaction mixture and extraction was carried out with ether. The ether layer was washed with water and it was extracted with 5% aqueous solution of potassium hydroxide. The aqueous layer was then acidified with hydrochloric acid and extracted again with ether. The ether layer was washed with water and it was dried with anhydrous sodium sulfate. The ether was then evaporated off under reduced-pressure. α-(3-Benzoylphenyl)propionic acid (ketoprofen) was obtained by recrystallization from benzene/petroleum ether mixture.

The spectrum and melting point were the same as those of an authentic sample.

EXPERIMENT 4

Synthesis of α-(3-Benzylphenyl)propionic Acid
Methyl Ester (Formula I: X=—OCH$_3$)

A mixture of 40 g of (3-vinylphenyl)phenylmethane obtained in Experiment 1, 150 ml of 5% hydrogen chloride solution in methyl alcohol, and 1 g of bistriphenylphosphine dichloropalladium was pressurized up to 300 kg/cm$^2$ with carbon monoxide. After the temperature was raised to 90° C. by heating, the pressure was raised to 700 kg/cm$^2$ with carbon monoxide. The reaction was continued until the absorption of carbon monoxide owing to the reaction was not observed.

After the reaction, the autoclave was cooled, unreacted gases were exhausted, and 1 g of potassium carbonate powder was added to the contents. The contents were then subjected to reduced-pressure distillation to obtain α-(3-benzylphenyl)propionic acid methyl ester (formula I, X=—OCH$_3$) was obtained. The yield was 90% on the basis of (3-vinylphenyl)phenylmethane. Analytical data are shown in the following.

Boiling Point: 118.2–120.2° C./0.5–1.0 mmHg
IR: (Neat) cm$^{-1}$: 3050, 2985, 1740, 1605, 1500, 1440, 1350, 1250, 1200, 1080, 1035, 1005, 790, 705
$^1$H-NMR: (CCl$_4$, δppm): 6.40–7.40, (9H Multiplet), 3.68, (2H Singlet), 3.10–3.65, (4H Multiplet), 1.32–1.51, ( 3H Doublet).
Elemental Analysis: (as C$_{17}$H$_{18}$O$_2$): Calculated: C: 80.31%, H: 7.09%, O: 12.60%, Found: C: 80.35%, H: 7.10%, O: 12.55%.

Unreacted (3-vinylphenyl)phenylmethane and (3-ethylphenyl)phenylmethane were contained in the separately recovered fraction of 283° to 293° C. of atmospheric pressure basis but this could be recycled to the dehydrogenation step.

Experiment 5

Synthesis of α-(3-Benzoylphenyl)propionic Acid
(Ketoprofen) - (2)

A solution of 25.4 g of α-(3-benzylphenyl)propionic acid methyl ester obtained in Experiment 4 in 200 ml of benzene was dispersed in 200 ml of water, to which 2 liter of 1.6% solution of potassium permanganate was added dropwise with stirring. After the dropping, stirring were continued for about 10 hours at room temperature. The mixture was then acidified with concentrated sulfuric acid and was treated with 30 g of sodium sulfite. After that, water was added to the reaction mixture and extraction was carried out with ether. The ether layer was washed with water and the ether was removed by reduced pressure evaporation. It was then subjected to hydrolysis with 5% aqueous solution of potassium hydroxide at refluxing temperature for 3 hours. After cooling, oily contents were washed and extracted with ether and the aqueous layer was acidified with hydrochloric acid and it was extracted again with ether. The ether layer was washed with water and dried with anhydrous sodium sulfate. The ether was then evaporated off under reduced-pressure. α-(3-Benzoylphenyl)propionic acid (ketoprofen) was obtained by recrystallization from benzene/petroleum ether. The spectrum and melting point were the same as those of an authentic sample.

EXPERIMENT 6

Synthesis of α-(3-Benzylphenyl)propionaldehyde (Formula I-a) - (1)

To a 500 ml autoclave with a stirrer were added 30 g of a fraction containing (3-vinylphenyl)phenylmethane obtained in Experiment 1 and 0.3 g of rhodiumhydridocarbonyl tristriphenylphosphine, and it was heated to a temperature of 60° C. and pressurized to 50 kg/cm$^2$ with an equimolar mixture of hydrogen and carbon monoxide. The reaction was continued until the absorption of the mixed gases owing to the reaction was not observed. After the reaction, it was cooled to room temperature and the remained mixed gases were exhausted. The contents were then placed into a reduced-pressure distillation column and α-(3-benzylphenyl)propionaldehyde (formula I-a) of 113° to 116° C./0.5-1 mmHg in boiling temperature range was obtained in a yield of 95%. The results of spectrum analysis are as follows:

IR: (Neat) cm$^{-1}$: 3050, 2990, 2840, 2720, 1735, 1600, 1500, 1450, 1390, 1090, 1010, 780, 700

1H-NMR: (CCl$_4$, δppm): 9.75, (1H Singlet), 6.65-7.65, (9H Multiplet), 2.95-3.50, (3H Multiplet), 1.35-1.50, (3H Doublet). Elemental Analysis: (as C$_{16}$H$_{16}$O): Calculated: C: 85.72%, H: 7.14%, O: 7.14%, Found: C: 85.70%, H: 7.15%, O: 7.15%.

EXPERIMENT 7

Synthesis of α-(3-Benzylphenyl)propionaldehyde (Formula I-a) - (2)

The hydroformylation of (3-vinylphenyl)phenylmethane was carried out in the like manner as in Experiment 6 using 0.1 g of rhodium oxide and 0.6 g of triphenylphosphine were used in place of rhodiumhydridocarbonyl tristriphenylphosphine. As a result, α-(3-benzylphenyl)propionaldehyde (formula 1-a) was obtained in a yield of 90%.

EXPERIMENT 8

Synthesis of Ketoprofen (Simultaneous Oxidation)

A solution of 20 g of α-(3-benzylphenyl)propionaldehyde (formula I-a) obtained in Experiment 6 in 200 ml of benzene was dispersed in 200 ml of water, to which 4 liter of 1.6% solution of potassium permanganate was added dropwise with stirring. After the dropping, stirring was continued for about 10 hours at room temperature.

The mixture was then acidified with concentrated sulfuric acid and it was treated with 60 g of sodium sulfite. Water was added to the reaction mixture and extraction was carried out with ether. The ether layer was washed with water and it was extracted with 5% aqueous solution of potassium hydroxide. The aqueous layer was then acidified with hydrochloric acid and it was extracted again with ether. The ether layer was washed with water and dried with anhydrous sodium sulfate. The ether was then evaporated off under reduced-pressure. α-(3-Benzoylphenyl)propionic acid (ketoprofen) was obtained by recrystallization from benzene/petroleum ether. The spectrum and melting point were the same as those of an authentic sample.

Industrial Applicability

As described above, the method of the present invention relates to the preparation of α-(3-benzylphenyl)propionic acid derivative which is the precursor of the anti-inflammatory medicine or pain-killing medicine of ketoprofen (trade name). It is useful as the ketoprofen can be prepared by a simple method such as oxidation by using the compound.

We claim:

1. A process for preparing α-(3-benzylpropionic acid derivative, which comprises the steps of: obtaining a reaction product comprising unreacted benzene, ethylbenzene, polyethylbenzene and heavier components by alkylating benzene with ethylene in the presence of ZSM-5 type synthetic zeolite catalyst, then recovering by distillation a fraction containing main components of 288° to 295° C. in boiling point, atmospheric pressure basis, from said reaction product, further dehydrogenating said fraction in the presence of a dehydrogenation catalyst, carbonylating the product with carbon monoxide and hydrogen or carbon monoxide and water or a lower alcohol in the presence of a transition metal complex carbonylation catalyst at a reaction temperature of 40° to 200° C., and recovering α-(3-benzylphenyl)propionic acid derivative represented by the following formula (I),

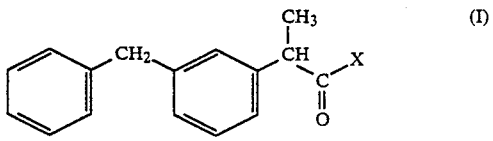

by means of distillation, extraction or combination thereof.

2. The method of claim 1, wherein said dehydrogenation catalyst is iron oxide, chromium oxide or mixtures thereof.

3. The method in claim 1, wherein the metal of said transition metal complex carbonylation catalyst is a transition metal selected from Pd, Pt, RH, IR and Ru.

4. The method in claim 1, wherein the temperature of said dehydrogenation is 500° to 700° C. and the pressure is reduced pressure to 5 kg/cm$^2$.

* * * * *

UNITED STATES PATENT AND TRADEMARK OFFICE
CERTIFICATE OF CORRECTION

PATENT NO. : 4,999,450

DATED : March 12, 1991

INVENTOR(S) : Isoo Shimizu, et al.

It is certified that error appears in the above-identified patent and that said Letters Patent is hereby corrected as shown below:

Column 15, line 9: "1H-NMR" should read as --$^{1}$H-NMR--

Column 16, line 44, Claim 3: "RH, IR" should read as --Rh, Ir--

Signed and Sealed this

Twenty-fifth Day of August, 1992

*Attest:*

DOUGLAS B. COMER

*Attesting Officer*     *Acting Commissioner of Patents and Trademarks*